United States Patent [19]

Wellinghoff et al.

[11] Patent Number: 5,888,528
[45] Date of Patent: Mar. 30, 1999

[54] SUSTAINED RELEASE BIOCIDAL POWDERS

[75] Inventors: Stephen T. Wellinghoff, San Antonio, Tex.; Sumner A. Barenberg, Chicago, Ill.; Hong Dixon, San Antonio, Tex.; Joel J. Kampa, Burnett, Tex.

[73] Assignee: Bernàrd Technologies, Inc., Chicago, Ill.

[21] Appl. No.: 858,859

[22] Filed: May 19, 1997

[51] Int. Cl.⁶ .......................... A01N 25/12; A01N 25/14; A01N 25/72; A01N 25/76

[52] U.S. Cl. .......................... 424/405; 424/408; 424/409; 424/420; 424/421; 424/497; 424/498; 424/501; 424/502; 252/187.21; 252/187.23; 252/188.21; 514/772; 514/772.3

[58] Field of Search .................................. 424/405, 408, 424/409, 420, 421, 497, 498, 501, 502; 252/187.21, 187.23, 188.21; 514/772, 772.3

[56] References Cited

U.S. PATENT DOCUMENTS

| | | |
|---|---|---|
| 2,071,625 | 5/1937 | Haas et al. .................................. 99/172 |
| 2,482,891 | 9/1949 | Aston ...................................... 252/187 |
| 2,546,568 | 3/1951 | Taylor ...................................... 99/150 |
| 2,558,942 | 7/1951 | Eagleson .................................. 167/30 |
| 3,183,057 | 5/1965 | Marks et al. ............................... 21/58 |
| 3,585,147 | 6/1971 | Gordon .................................... 252/187 |
| 3,591,515 | 7/1971 | Lovely .................................... 252/187 |
| 3,767,787 | 10/1973 | Segal ........................................ 424/76 |
| 4,104,190 | 8/1978 | Hartshorn ............................ 252/187 R |
| 4,330,531 | 5/1982 | Alliger .................................... 424/149 |
| 4,499,077 | 2/1985 | Stockel et al. ........................... 424/149 |
| 4,504,442 | 3/1985 | Rosenblatt et al. ........................ 422/37 |
| 4,547,381 | 10/1985 | Mason et al. ............................ 426/316 |
| 4,585,482 | 4/1986 | Tice et al. .............................. 106/15.05 |
| 4,681,739 | 7/1987 | Rosenblatt et al. ........................ 422/37 |
| 4,689,169 | 8/1987 | Mason et al. ........................ 252/186.24 |
| 4,728,498 | 3/1988 | Theeuwes ................................. 422/29 |
| 4,748,904 | 6/1988 | Razeto et al. ............................. 99/467 |
| 4,829,129 | 5/1989 | Kelley .................................... 525/326.9 |
| 4,880,638 | 11/1989 | Gordon .................................... 424/662 |
| 4,889,654 | 12/1989 | Mason et al. ............................. 252/100 |
| 4,891,216 | 1/1990 | Kross et al. ............................... 424/78 |
| 4,925,645 | 5/1990 | Mason ...................................... 423/477 |
| 4,956,184 | 9/1990 | Kross ...................................... 424/661 |
| 4,966,775 | 10/1990 | Donofrio et al. ......................... 424/661 |
| 4,975,109 | 12/1990 | Friedman, Jr. et al. ..................... 71/67 |
| 4,986,990 | 1/1991 | Davidson et al. ........................ 424/665 |
| 5,116,575 | 5/1992 | Badertscher et al. ....................... 422/28 |
| 5,126,070 | 6/1992 | Leifheit et al. ..................... 252/186.36 |
| 5,252,343 | 10/1993 | Kross ...................................... 424/661 |
| 5,306,440 | 4/1994 | Ripley et al. ....................... 252/186.33 |
| 5,360,609 | 11/1994 | Wellinghoff .......................... 514/772.3 |
| 5,384,134 | 1/1995 | Kross et al. ............................. 424/661 |
| 5,387,350 | 2/1995 | Mason ...................................... 210/754 |
| 5,399,288 | 3/1995 | Marzouk et al. .................... 252/186.21 |
| 5,405,549 | 4/1995 | Pitochelli ........................... 252/187.21 |
| 5,650,446 | 7/1997 | Wellinghoff et al. ................ 514/772.3 |

FOREIGN PATENT DOCUMENTS

| | | |
|---|---|---|
| 1 048 200 | 1/1991 | China . |
| 0 287 074 | 4/1988 | European Pat. Off. . |
| 0 611 162 | 2/1994 | European Pat. Off. . |
| 0 611 163 | 2/1994 | European Pat. Off. . |
| 57/198775 | 12/1982 | Japan . |
| 60/092759 | 5/1985 | Japan . |
| 04/164005 | 6/1992 | Japan . |
| 6-107971 | 4/1994 | Japan . |
| 2151138 | 12/1984 | United Kingdom . |
| WO 85/04107 | 3/1985 | WIPO . |
| WO 88/09176 | 5/1988 | WIPO . |
| WO 96/18300 | 6/1996 | WIPO . |

*Primary Examiner*—Peter O'Sullivan
*Attorney, Agent, or Firm*—Senniger, Powers, Leavitt & Roedel

[57] ABSTRACT

A powder for sustained release of a gas including a hydrophilic core, a hydrophobic layer on an outer surface of the hydrophilic core, and particles in contact with the hydrophobic layer. The hydrophobic layer contains an acid releasing agent. The particles contain an anhydrous material capable of binding with water. The core, the particles, and the hydrophobic layer are substantially free of water, and the core is capable of generating and releasing a gas after hydrolysis of the acid releasing agent.

65 Claims, 3 Drawing Sheets

SUSTAINED RELEASE BIOCIDAL POWDERS

BACKGROUND OF THE INVENTION

The present invention relates generally to a powder that provides sustained release of a gas. The invention particularly relates to a powder for retarding, controlling, killing or preventing microbiological contamination (e.g., bacteria, fungi, viruses, mold spores, algae, and protozoa), deodorizing and/or retarding, preventing or controlling chemotaxis by release of a gas, such as chlorine dioxide, sulfur dioxide, nitrogen dioxide, nitric oxide, nitrous oxide, carbon dioxide, hydrogen sulfide, hydrocyanic acid, dichlorine monoxide, or chlorine.

Chlorine dioxide ($ClO_2$) is a superior oxidizing agent widely used as a bleach, disinfectant, fumigant or deodorizer. It can penetrate the cell wall or membrane and cytoplasm of mold spores, bacteria and other microbiological contaminants at concentrations below one part per million and destroy them.

The incorporation of chlorine dioxide or sodium chlorite in food packaging has prompted studies to determine whether residual levels of such preservatives result in a significant genetic or carcinogenic hazard to humans. Meier et al. studied the effect of subchronic and acute oral administration of chlorine, chlorine dioxide, sodium chlorite and sodium chlorate on the induction of chromosomal aberrations and spermhead abnormalities in mice [Environ. Mutagenesis, 7, 201 (1985)]. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Vilagines et al. attribute the relatively innocuous effect of chlorine dioxide to its inability to produce halomethanes, unlike hypochlorite and chlorine [Proc. AWWA Disinfect. Semin., 24 pp. (1977); Chem. Abs. 93, 173513f]. Recently, Richardson et al. reported that an extensive study of the reaction of chlorine dioxide with water borne organics by the Environmental Protection Agency confirmed this observation [Environ. Sci. Technol., 28, 592 (1994)].

Japanese Kokai Nos. 63/296,758, 63/274,434, and 57/168,977 describe deodorants containing chlorine dioxide incorporated in a polymer, ceramic beads, or calcium silicate wrapped in nonwoven cloth, respectively. Gels that generate chlorine dioxide for use as topical applications for disinfection are disclosed by Kenyon et al., Am. J. Vet. Res., 45(5), 1101 (1986). Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice et al., U.S. Pat. No. 4,585,482 describe gradual hydrolysis of alternating poly(vinyl methyl ether-maleic anhydride) or poly(lactic-glycolic acid) to generate acid that can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule. Solvents are required for reaction and application of the capsules. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems.

Powders that release chlorine dioxide as soon as they are prepared have been formed by mixing acid solids and chlorite solids. Lovely, U.S. Pat. No. 3,591,515 describes a chlorite-containing powder that releases chlorine dioxide upon being admixed with an acid-containing powder Hartshorn, U.S. Pat. No. 4,104,190 describes solid mixtures of sodium chlorite and citric, adipic or malic acid that are compressed to form tablets. Mason et al., U.S. Pat. Nos. 4,547,381 and 4,689,169 disclose mixtures of powdered sodium chlorite, acid and inert diluent that release chlorine dioxide without exposing the mixtures to ambient moisture. Tice et al., U.S. Pat. No. 4,585,482 describe solid admixtures of sodium chlorite and polylactic acid.

Wellinghoff et al. have formulated composites that include a hydrophobic phase containing an acid releasing agent and a hydrophilic phase containing chlorite anions. The composite is substantially free of water and gas (e.g., chlorine dioxide) until it is exposed to moisture. Once exposed to moisture, acid and hydronium ions are generated in the hydrophobic phase. The hydronium ions migrate to the hydrophilic phase and react with chlorite anions to generate chlorine dioxide from the composite. These composites are composed of and generate only substances used in foods or substances generally recognized as safe or inert substances. The composites can be used for food packaging and other applications where the substances can be ingested by or in contact with humans. These composites are described in U.S. Pat. No. 5,360,609 and copending U.S. patent application Ser. Nos. 08/465,358, 08/465,086, 08/462,164, 08/461,716, and 08/461,304.

Wellinghoff et al. U.S. patent application Ser. No. 08/462,039 discloses a composite formulated for maximum chlorine dioxide release in which the hydrophilic material contains an α-amino ether, ester or alcohol and a chlorite salt formed by reaction of an iminium chlorite and a base. Iminium chlorite is unstable to nucleophilic attack by the chlorite anion. When the iminium chlorite is reacted with a base, however, the more stable α-amino ether, ester or alcohol and a chlorite salt are formed.

Wellinghoff et al. U.S. patent application Ser. No. 08/461,706 describes a method for maximizing chlorine dioxide release from an amine-containing composite by omitting the chlorite source until the composite is applied to a surface. After application, the composite is exposed to chlorine dioxide gas that either reacts with the amine to form iminium chlorite in situ or reacts with the amine to provide chlorite anions. The composite is then activated in the presence of moisture to release chlorine dioxide. The composite can be exposed to elevated temperatures during processing, storage and application because the hydrophilic material does not contain iminium chlorite or any chlorite anions that could decompose at such temperatures. The method also precludes premature release of chlorine dioxide from the composite.

Barenberg et al. U.S. patent application Ser. No. 08/465,087 describes numerous methods of using composites such as those disclosed by Wellinghoff et al. to retard bacterial, fungal, and viral contamination and growth of molds on food, produce, meat, and other materials and to deodorize materials such as textiles and storage spaces.

Wellinghoff et al. U.S. patent application Ser. No. 08/651,876 describes transparent compositions that provide sustained release of chlorine dioxide.

There is a need for an inert powder that can be easily activated to initiate release of chlorine dioxide or another biocidal or deodorizing gas in use. A powder that is composed of and generates only substances used in foods, or those generally recognized as safe or inert substances, is particularly needed for food packaging and other applications where the substances can be ingested by or in contact with humans. Although the Wellinghoff et al. composites are effective biocides, there is a need for biocidal compositions that can be more readily manufactured and provide more control or flexibility for sustained release of a gas.

Summary of the Invention

Among the objects of the invention, therefore, may be noted the provision of a powder that releases a concentration of chlorine dioxide or other biocidal gas sufficient to eliminate bacteria, fungi, molds, algae, protozoa and viruses; the provision of such a powder that releases such chlorine dioxide concentrations after activation for a period of up to several months; the provision of such a powder that is free-flowing and can be easily blended with other ingredients prior to application; the provision of such a powder that can penetrate porous surfaces; the provision of such a powder that increases the release rate of chlorine dioxide in proportion to increased temperature and humidity, which promote mold and bacteria growth; and the provision of such a powder that only releases substances approved for human exposure or ingestion.

The present invention is directed to a powder for sustained release of a gas including a hydrophilic core, a hydrophobic layer on an outer surface of the hydrophilic core, and particles in contact with the hydrophobic layer. The hydrophobic layer contains an acid releasing agent. The particles contain an anhydrous material capable of binding with water. The core, the particles, and the hydrophobic layer are substantially free of water, and the core is capable of generating and releasing a gas after hydrolysis of the acid releasing agent.

Another embodiment of the present invention is a powder for sustained release of a gas comprising a hydrophilic core, a first hydrophobic layer containing an acid releasing agent, a second hydrophobic layer between the first hydrophobic layer and the hydrophilic core, and particles in contact with the first hydrophobic layer. The particles contain an anhydrous material capable of binding with water. The core, the particles, the first hydrophobic layer and the second hydrophobic layer are substantially free of water, and the core is capable of generating and releasing a gas after hydrolysis of the acid releasing agent.

Yet another embodiment of the invention is a powder for sustained release of chlorine dioxide comprising a hydrophilic core containing chlorite anions, a first hydrophobic layer containing an acid releasing wax, a second hydrophobic layer between the first hydrophobic layer and the hydrophilic core, and particles in contact with the first hydrophobic layer. The acid releasing wax has the formula wherein G has the formula $-(CR_2)_x-CR_3$ or wherein each R is individually selected from hydrogen, hydroxy, alkyl, alkenyl, or $-OC(O)R'$; R' is a $C_4$ to $C_{27}$ alkyl or $C_4$ to $C_{27}$ alkenyl; x is an integer from 1 to 30; y is an integer from 0 to 30; and z is an integer from 0 to 30. The second hydrophobic layer contains microcrystalline wax, paraffin wax, synthetic wax, or polymer. The particles contain an anhydrous material capable of binding with water. The core, the particles, the first hydrophobic layer and the second hydrophobic layer are substantially free of water, and the core is capable of releasing chlorine dioxide gas upon hydrolysis of the acid releasing agent.

Another embodiment of the invention is directed to a method of retarding, killing, preventing or controlling microbiological contamination on a surface of a material, within the material or in the atmosphere surrounding the material, by exposing a surface of a material to the powder, and exposing the surface to moisture to generate and release a biocidal gas from the powder into the atmosphere surrounding the surface.

The invention is also directed to a method of retarding, killing, preventing or controlling microbiological contamination on a surface of a material, within the material or in the atmosphere surrounding the material, by placing the material adjacent the powder, and exposing the powder to moisture to release a biocidal gas from the powder into the atmosphere surrounding the material.

The invention is also directed to a method of deodorizing a surface of a material or the atmosphere surrounding the material, by exposing a surface of a material to the powder, and exposing the surface to moisture to generate and release a deodorizing gas from the powder into the atmosphere surrounding the surface.

Yet another embodiment of the invention is directed to a method of deodorizing a surface of a material or the atmosphere surrounding the material, by placing the material adjacent the powder, and exposing the powder to moisture to release a deodorizing gas from the powder into the atmosphere surrounding the material.

Another embodiment of the invention is directed to a method of retarding, preventing or controlling chemotactic attraction of an organism to a material, by exposing a surface of a material to the powder, and exposing the surface to moisture to generate and release an odor-masking gas from the powder into the atmosphere surrounding the surface.

Figure 2:
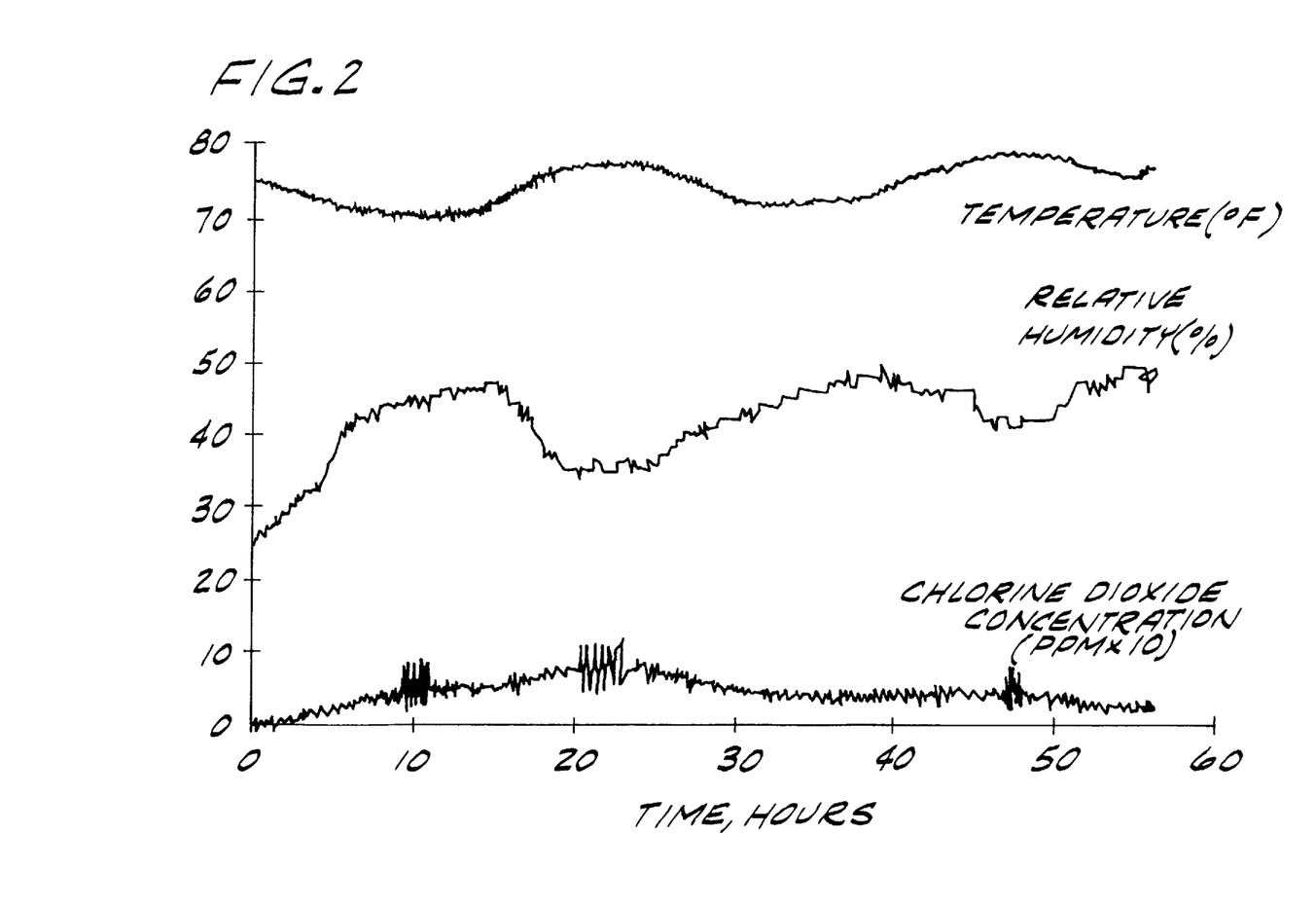

The invention is also directed to a method of retarding, preventing or controlling chemotactic attraction of an organism to a material, by placing the material adjacent the powder, and exposing the powder to moisture to release an odor-masking gas from the powder into the atmosphere surrounding the material.

The invention is also directed to a process for preparing a powder providing sustained release of a gas, by providing a hydrophobic liquid containing an acid releasing agent, admixing hydrophilic particles containing anions into the hydrophobic liquid to form coated hydrophilic particles, admixing anhydrous particles with the coated hydrophilic particles to form a product, cooling the product, and fragmenting the product to form a powder.

Another embodiment of the invention is directed to a process for preparing a powder providing sustained release of a gas, by providing a hydrophobic liquid, admixing hydrophilic particles containing anions into the hydrophobic liquid to form coated hydrophilic particles, admixing a hydrophobic material containing an acid releasing agent with the coated hydrophilic particles to form an intermediate powder, admixing the intermediate powder with anhydrous particles to form a product, cooling the product, and fragmenting the product to form a powder.

Other objects and advantages of the invention will be apparent from the following detailed description.

BRIEF DESCRIPTION OF THE DRAWINGS

FIGS. 1*a* and 1*b* are schematics of powders for providing sustained release of a gas; and FIGS. 2 and 3 are plots of chlorine dioxide concentration, temperature, and humidity as a function of time for a powder composition.

DETAILED DESCRIPTION OF THE PREFERRED EMBODIMENTS

In accordance with the present invention, it has been discovered that sustained release of a gas can be generated from a powder containing a hydrophilic core encased within a hydrophobic layer when the powder is exposed to moisture. Release of gas from the powder is controlled by surrounding the hydrophilic core with a hydrophobic material and/or a dispersant. The powder is easily prepared and can be used as is or incorporated into various end-use products, such as films, formed objects, adhesives, granular blends, and powdered compositions.

In one embodiment of the invention shown in FIG. 1a, the powder 10 is comprised of a hydrophilic core 12 having a hydrophobic layer 14 on an outer surface 16 of the core 12. The hydrophobic layer 14 contains an acid releasing agent. Particles 18 contact the hydrophobic layer 14 of the powder 10. The particles contain an anhydrous material capable of binding with water. For purposes of the present invention, an anhydrous material does not contain water, such as adsorbed water or water of crystallization. Although the hydrophobic layer is preferably continuous and substantially uniform, a powder having a discontinuous hydrophobic layer of variable thickness provides acceptable, sustained release of a gas.

In a preferred embodiment of the invention illustrated in FIG. 1*b*, the powder 10 includes a second hydrophobic layer 20 separating the hydrophilic core 12 from the first hydrophobic layer 14. The hydrophobic layer 20 controls release of gas from the powder. Thus, a preferred powder of the invention is comprised of a hydrophilic core 12 having a hydrophobic layer 20 on an outer surface 16 of the core 12, and a hydrophobic layer 14 on an outer surface 22 of the hydrophobic layer 20. The hydrophobic layer 14 contains an acid releasing agent. Particles 18 contact the hydrophobic layer 14 of the powder 10. The particles contain an anhydrous material capable of binding with water. Although each of the hydrophobic layers is preferably continuous and substantially uniform, a powder having discontinuous hydrophobic layers of variable thickness provides acceptable, sustained release of a gas.

When a powder of the invention is exposed to ambient moisture or otherwise contacted with water, the water binds to the particles 18 on the outer surface of the powder, and diffuses into the hydrophobic layer 14 containing the acid releasing agent. The acid releasing agent is either an acid or a substance that can be hydrolyzed to an acid (i.e., a substance that reacts with the water that diffuses into the hydrophobic layer to form an acid). In either case, the acid in the hydrophobic layer 14 dissolves in the water that diffuses into the layer, forming hydronium ions and a counterion. The reaction products of this hydrolysis reaction are hydronium ions and counterions when the reaction proceeds to completion, or hydronium ions, counterions, acid and water when the reaction is in equilibrium. The hydronium ions resulting from the acid hydrolysis diffuse from the hydrophobic layer 14 into the hydrophilic core 12, where they react with anions to generate a gas. The gas diffuses out of the powder into the surrounding atmosphere for a period of up to about six months to affect materials situated near the powder. Powders that release at least about $1.0\times10^{-6}$ mole gas/$cm^2$ for a period of at least one week, one month or six months can be formulated by the processes of the present invention for a variety of end uses, including deodorization, chemotaxis control, delay or prevention such as reduction of insect infestation, and control, delay, destruction or prevention of the growth of microorganisms such as bacteria, molds, fungi, algae, protozoa, and viruses on materials.

The hydrophobic layers 14 and 20, hydrophilic core 12 and the particles 18 are substantially free of water to avoid release of gas prior to use of the powder. For purposes of the present invention, the hydrophilic core, the hydrophobic layers, and the particles are substantially free of water if the amount of water in the powder does not provide a pathway for transmission of hydronium ions from the hydrophobic layer containing the acid releasing agent to the hydrophilic core. Preferably, each of the hydrophilic core, the hydrophobic layers and the total particles 18 embedded in the hydrophobic layer can include up to about 0.1 wt. % water and, more preferably up to about 0.05 wt. % water, without providing such a pathway for interdiffusion between the hydrophilic core and the hydrophobic layer. Insubstantial amounts of water can hydrolyze a portion of the acid releasing agent to produce acid and hydronium ions within the hydrophobic layer. The hydronium ions, however, do not diffuse into the hydrophilic core until enough free water is present for transport of hydronium ions.

When the hydrophilic core 12 is coated with a hydrophobic layer 20 as shown in FIG. 1*b*, this hydrophobic layer controls release of gas from the powder. Release of the gas is controlled because the hydronium ions produced in the hydrophobic layer 14 must diffuse through the hydrophobic layer 20 to react with anions within the hydrophilic core. Release of a gas does not occur until enough moisture is adsorbed to provide a pathway for interdiffusion between the hydrophilic core and the hydrophobic layers.

The powder can include coatings between the hydrophilic core 12 and the hydrophobic layers 14 and 20 so long as the coatings do not prevent the diffusion of hydronium ions from the hydrophobic layer to the hydrophilic core or diffusion of gas from the powder.

The rate of gas release from a powder and the release rate profile (as shown in FIG. 2 for example) can be altered in various ways, such as by changing the temperature of the powder, changing the concentration of acid releasing agent in the powder, adding a desiccant or humectant to the powder to control release of gas once the powder is exposed to moisture, adding a buffer to the hydrophobic material to delay release of a gas from the powder, changing the hydrophobicity of the hydrophobic material by changing the nature of the acid generative moiety therein, changing the powder microstructure, substituting alternative hydrophobic materials or anhydrous particles, changing the method of processing the powder, or changing the order of addition of ingredients in preparing the powder.

Preferably, the powder comprises between about 0.1 wt. % and about 10 wt. % hydrophilic core, between about 5 wt. % and about 80 wt. % hydrophobic material, and between about 10 wt. % and about 99 wt. % of the particles. More preferably, the powder comprises between about 1 wt. % and about 5 wt. % hydrophilic core, between about 20 wt. % and about 70 wt. % hydrophobic material, and between about 30 wt. % and about 80 wt. % of the particles.

When the powder includes one hydrophobic layer, the hydrophobic material preferably contains between about 3 wt. % and 100 wt. % acid releasing agent, up to 20 wt. % diluent and up to about 20 wt. % dispersant, and, more preferably, between about 10 wt. % and about 60 wt. % acid releasing agent, between about 10 wt. % and about 20 wt. % diluent and between about 1 wt. % and about 10 wt. % dispersant.

When the powder includes first and second hydrophobic layers, the first hydrophobic layer preferably contains between about 3 wt. % and 100 wt. % acid releasing agent, up to about 20 wt. % diluent and up to about 20 wt. % dispersant, and the second hydrophobic layer preferably contains up to 100 wt. % diluent and up to 100 wt. % dispersant. More preferably, the first hydrophobic layer contains between about 10 wt. % and about 60 wt. % acid releasing agent, between about 40 wt. % and about 90 wt. % diluent and between about 0.1 wt. % and about 10 wt. % dispersant, and the second hydrophobic layer contains up to about 10 wt. % diluent and between about 90 wt. % and 100 wt. % dispersant.

The hydrophilic core of the powder contains a salt composed of anions, which react with hydronium ions to form the gas, and counterions. Preferred salts include sodium, potassium, calcium, lithium or ammonium salts of a chlorite, bisulfite, hydrosulfide, bicarbonate, hypochlorite, nitrite, or cyanide. The hydrophilic core particles are commercially available from various sources, including Vulcan Chemicals, Fisher and Aldrich. The core particles preferably have a diameter of between about 1 and about 300 microns.

The hydrophilic core is generally composed of the salt that reacts to form the gas and not more than about 30 wt. % of other salts.

The gas released by the powder will depend upon the anions within the hydrophilic core. Any gas that is formed by reaction of a hydronium ion and an anion can be generated and released by the powder. The gas is preferably chlorine dioxide, sulfur dioxide, hydrogen sulfide, hydrocyanic acid, nitrogen dioxide, nitric oxide, nitrous oxide, carbon dioxide, dichlorine monoxide, or chlorine.

Chlorine dioxide gas is released if the hydrophilic core contains a source of chlorite anions. Suitable chlorite sources that can be incorporated into the hydrophilic core include alkali metal chlorites such as sodium chlorite or potassium chlorite, alkaline-earth metal chlorites such as calcium chlorite, or chlorite salts of a transition metal ion or a protonated primary, secondary, tertiary or quaternary amine such as ammonium chlorite, trialkylammonium chlorite, and quaternary ammonium chlorite Many chlorite sources, such as sodium chlorite, are stable at processing temperatures in excess of about 100° C., allowing for processing at relatively high temperatures. Chlorine dioxide-releasing powders can be used to deodorize, retard, prevent or control chemotaxis, or to kill, retard, control or prevent the growth of bacteria, molds, fungi, algae, protozoa, and viruses.

Sulfur dioxide is released if the hydrophilic core contains bisulfite anions. Bisulfite sources that can be incorporated into the hydrophilic core include alkali metal bisulfites such as sodium bisulfite or potassium bisulfite, alkaline-earth metal bisulfites such as calcium bisulfite, or bisulfite salts of a transition metal ion or a protonated primary, secondary, tertiary or quaternary amine. Sulfur dioxide gas-releasing powders can be used for food preservation (e.g. to inhibit browning of produce), disinfection, and inhibition of enzyme-catalyzed reactions. The powders can also be used for reduction of chlorine gas concentration in catalytic cycles where aluminum or iron powder is used to selectively scrub chlorine from a mixture of chlorine and chlorine dioxide. The powders are also useful in modified atmosphere packaging by placing the powder within a package and sealing the package to create a sulfur dioxide atmosphere within the package.

Hydrogen sulfide is released from a hydrophilic core containing hydrosulfide anions. Acceptable sources of hydrosulfide anions include alkali metal hydrosulfides such as sodium hydrosulfide or potassium hydrosulfide, alkaline-earth metal hydrosulfides such as calcium hydrosulfide, or hydrosulfide salts of a transition metal ion or a protonated primary, secondary, tertiary or quaternary amine. Hydrogen sulfide gas-releasing powders can be used as a reducing agent or a sulfur source in the manufacture of chemicals, and as a polymerization inhibitor.

Chlorine gas and dichlorine monoxide are released from a hydrophilic core containing hypochlorite anions Acceptable sources of hypochlorite anions include alkali metal hypochlorites such as sodium hypochlorite, alkaline-earth metal hypochlorites such as calcium hypochlorite, or hypochlorite salts of a transition metal ion or a protonated primary, secondary, tertiary or quaternary amine. Chlorine gas-releasing powders can be used in processing meat, fish and produce and as an insecticide. Dichlorine monoxide releasing powders can be used as a biocide.

Hydrocyanic acid is released from the hydrophilic core if it contains a source of cyanide anions. Suitable sources of cyanide anions include alkali metal cyanides such as sodium cyanide or potassium cyanide, alkaline-earth metal cyanides such as calcium cyanide, or cyanide salts of a transition metal ion or a protonated primary, secondary, tertiary or quaternary amine. Hydrocyanic acid gas-releasing powders can be used as a pesticide or a rodenticide.

Carbon dioxide and dichlorine monoxide gas are released if the hydrophilic core contains a source of bicarbonate anions. Suitable bicarbonate sources that can be incorporated into the hydrophilic core include alkali metal bicarbonates such as sodium bicarbonate, potassium bicarbonate, or lithium bicarbonate, alkaline-earth metal bicarbonates, or bicarbonate salts of a transition metal ion or a protonated primary, secondary, tertiary or quaternary amine such as ammonium bicarbonate. Carbon dioxide gas-releasing powders can be used in greenhouses by applying it to the soil surface to enrich the air surrounding plants. The carbon dioxide-releasing powders can also be used in modified atmosphere packaging by placing the powder within a package and sealing the package to create a carbon dioxide atmosphere within the package.

Nitrogen dioxide and nitric oxide are released from the hydrophilic core if it contains a source of nitrite anions. Suitable sources of nitrite anions include alkali metal nitrites such as sodium nitrite or potassium nitrite, alkaline-earth metal nitrites such as calcium nitrite, or nitrite salts of a transition metal ion or a protonated primary, secondary, tertiary or quaternary amine. Nitrogen dioxide or nitric oxide gas-releasing powders can be used to improve biocompatibility of biomaterials and for modified atmosphere packaging.

Any acid releasing agent that is capable of being hydrolyzed by ambient moisture is acceptable for purposes of the present invention. Preferably, the acid releasing agent does not react with the hydrophilic core in the absence of moisture, and does not exude or extract into the environment. Suitable acid releasing agents include carboxylic acids, esters, anhydrides, acyl halides, phosphoric acid, phosphate esters, trialkylsilyl phosphate esters, dialkyl phosphates, sulfonic acid, sulfonic acid esters, sulfonic acid chlorides, phosphosilicates, phosphosilicic anhydrides, carboxylates of poly α-hydroxy alcohols such as sorbitan monostearate or sorbitol monostearate, and phosphosiloxanes. Examples of such acid releasing agents include an anhydride or phosphate ester blended with or grafted to polypropylene, polyethylene or polystyrene, or trimethylsilyl phosphate esters of the formulae

$(R_2)_{4-n}Si(OR_1)_n$ or $CH_3SiOP(O)(OR)_2$ wherein R is a non-hydrogen bonding group, alkyl or aryl, $R_1$, and $R_2$ are alkyl, alkoxy or aryl and n is 1-25.

Linear or star like oligomers (e.g., a micelle like molecule with a lipid wall and a P-O-Si core), such as a phosphosilicic anhydride that is the reaction product of a phosphoric acid ester of a $C_4$ to $C_{27}$ organic compound and a silicate ester, are preferred acid releasing agents. Preferred phosphosilicic anhydrides of esters have the formula wherein G is a carboxylic acid ester of a polyhydric alcohol and a $C_4$ to $C_{27}$ hydrocarbon, which has the formula wherein each R is individually selected from hydrogen, hydroxy, alkyl, alkenyl, or —OC(O)R'; R' is a $C_4$ to $C_{27}$ alkyl or $C_4$ to $C_{27}$ alkenyl; x is an integer from 1 to 30; y is an integer from 0 to 30; and z is an integer from 0 to 30. Particularly preferred phosphosilicic anhydrides of polyol based esters include alkylene glycol fatty acid ester acid releasing waxes such as propylene glycol monostearate acid releasing wax having the formula wherein G is

A preferred phosphosilicic anhydride of a glycerol based ester, known as LPOSI or glycerol monostearate acid releasing wax, has the formula wherein G has the formula Other preferred acid releasing agents have the formulae:

wherein $M(Y)_z$ is an oligomeric radical in which Y is a portion of a multifunctional oxide structure and M is a group IIIA, IVA, or IVB element such as titanium, aluminum, tin, or silicon;; $R_1$ is an alkyl group; $R_2$ is methyl, ethyl, propyl, a methyl amido, or an ethyl amido group; m is 0, 1, 2 or 3; n is 0, 1, 2 or 3; and z is 2 or 3.

Acid anhydrides are also preferred acid releasing agents and include organic acid anhydrides, mixed organic acid anhydrides, homopolymers of an organic acid anhydride or a mixed inorganic acid anhydride, and copolymers of an organic acid anhydride or a mixed inorganic acid anhydride with a monomer containing a double bond. Preferred mixed inorganic acid anhydrides contain a phosphorus-oxygen-silicon bond. Preferred anhydrides include copolymers of maleic anhydride, methacrylic anhydride, acetic anhydride, propionic anhydride, or succinic anhydride, and vinyl, styrene or an alkene, such as maleic anhydride-styrene copolymers, or grafts thereof with olefins such as polypropylenes, polyethylenes, or polystyrenes. Copolymers of acid anhydrides and esters of lactic or glycolic acids can provide a rapid initial gas release rate followed by a slow release rate.

The diluent in either or both of the hydrophobic layers is any hydrophobic material that can be applied to the hydrophilic core and solidified to form a layer on the core. Preferred diluents include microcrystalline wax, paraffin wax, synthetic wax such as chlorinated wax or polyethylene wax, or a polymer such as atactic polypropylene, polyolefin, or polyester, or polymer blends, multicomponent polymers such as copolymers or terpolymers, or polymer alloys thereof. The diluents are commercially available from various sources. Preferred microcrystalline waxes include the Petrowax microcrystalline waxes commercially available from Astor Wax Corp., Doraville, Ga.

The dispersant in either or both of the hydrophobic layers is any substance that minimizes agglomeration of the hydrophilic core particles during preparation of the powder, controls release of the gas from the powder, lowers the surface reactivity of the hydrophilic core, and does not react with the hydrophilic core. Substances having hydrophilic and hydrophobic portions are preferred. The hydrophilic portion of the substance can be absorbed by the surface of the hydrophilic core. The hydrophobic portion of the substance minimizes agglomeration of the hydrophilic core particles when the particles are mixed. Preferred dispersants that can be incorporated into the hydrophobic layers have a melting point not greater than 150° C., and include amides of carboxylates such as amide isostearates, polyvinyl acetates, polyvinyl alcohols, polyvinylpyrrolidone copolymers, and metal carboxylates such as zinc isostearate. Dispersants having a melting point greater than 50° C. are preferably admixed with the hydrophilic particles before being admixed with the hydrophobic material. Suitable polyvinylpyrrolidone copolymers include copolymers of polyvinylpyrrolidone and hexadecane such as Ganex V-216, and copolymers of polyvinylpyrrolidone and eicosene such as Ganex V-220, which are commercially available from GAF Corp.

The particles embedded in the outer layer of the powder contain an anhydrous material capable of binding with water. The particles act as moisture scavengers to minimize premature hydrolysis of the acid releasing agent in the hydrophobic layer. Suitable anhydrous materials include sodium sulfate, calcium sulfate, ferrous sulfate, magnesium sulfate, calcium chloride, moisture-depleted silica gel, alumina, zeolites, clays such as bentonite and kaolin, potassium permanganate, molecular sieves and oxygen-scavenging salts. The anhydrous particles are commercially available from numerous sources.

The anhydrous particles are preferably between about 1 and about 300 microns in diameter.

Figure 1A:
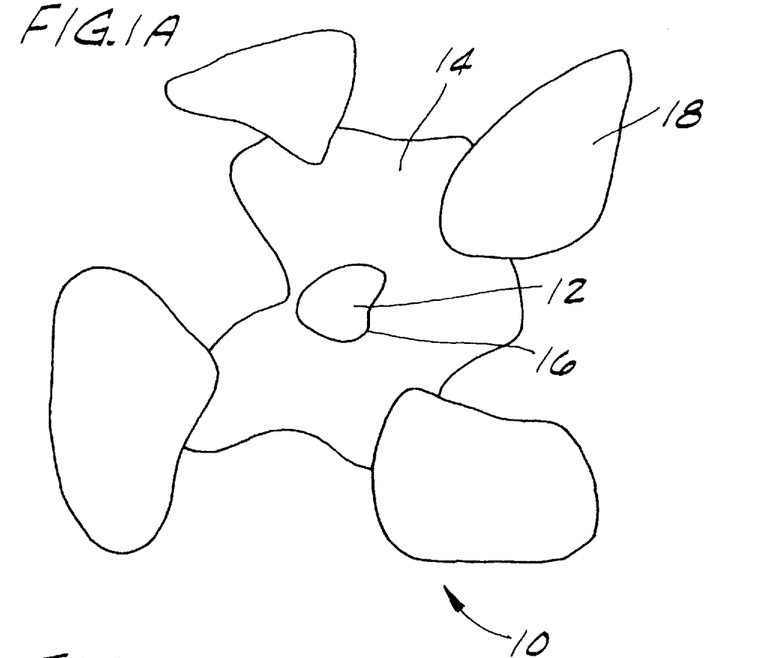

The powder shown in FIG. 1a is generally prepared by admixing the hydrophilic core particles containing anions into a hydrophobic liquid containing the acid releasing agent to form coated hydrophilic particles, admixing anhydrous particles with the coated hydrophilic particles to form a product, cooling the product, and fragmenting the product to form a powder. The hydrophobic liquid may include a dispersant as described above to prevent agglomeration of the hydrophilic particles.

The powders of the invention can also be prepared using fluidized beds, mechanical blending, mechanical-fluidized blending and other known powder preparation methods.

Figure 1B:
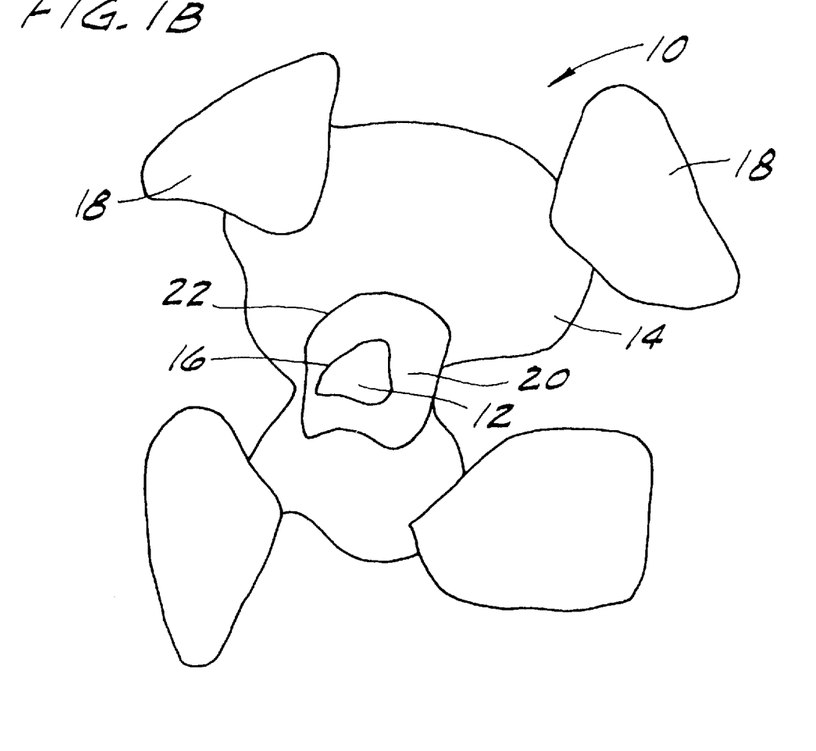

The powder illustrated in FIG. 1b is prepared by admixing hydrophilic core particles containing anions into a hydrophobic liquid to form coated hydrophilic particles, admixing a hydrophobic material containing an acid releasing agent with the coated hydrophilic particles to form an intermediate powder, admixing the intermediate powder with anhydrous particles to form a product, cooling the product, and fragmenting the product to form a powder. In a preferred embodiment, anhydrous particles are admixed with the coated hydrophilic particles before the hydrophobic material is added to form the intermediate powder. The hydrophobic liquid may include a dispersant as described above to prevent agglomeration of the hydrophilic particles.

In some instances, powders having a hydrophilic core containing two or more different anions are effective in controlling release of a gas. Either of the powders illustrated in FIGS. 1a or 1b, for example, can be prepared by admixing hydrophilic core particles containing chlorite anions and hydrophilic core particles containing bisulfite anions into the hydrophobic liquid to form the coated hydrophilic particles. If chlorine dioxide and sulfur dioxide are released in preparing the powder, the sulfur dioxide reduces the chlorine dioxide to chlorite, controlling release of chlorine dioxide from the powder. The presence of bisulfite anions in the hydrophilic core also delays chlorine dioxide release from the powder during storage to avoid reaction of chlorine dioxide with powder additives such as fragrances. Powders containing two or more different anions in the hydrophilic core can also release two or more different gases for different purposes. For example, a powder containing bisulfite and chlorite anions can release sulfur dioxide for food preservation and chlorine dioxide for deodorization of the food or control of chemotaxis.

The hydrophilic core particles and the anhydrous particles can be manufactured by conventional processes and packaged in dry sealed containers, or can be purchased from various sources. The particles and other ingredients are stored in a dry atmosphere before being used in the powder preparation process.

Although the hydrophilic and hydrophobic materials and the particles containing anhydrous material can be formulated as described above, it is preferred that the hydrophilic core contains an alkali metal chlorite or alkaline earth metal chlorite for release of chlorine dioxide. The first hydrophobic layer preferably includes a microcrystalline wax diluent and an acid releasing wax, such as propylene glycol monostearate acid releasing wax. The second hydrophobic layer preferably contains a microcrystalline wax diluent and a dispersant. The particles are preferably sodium sulfate or calcium sulfate.

The preferred phosphosilicic anhydride acid releasing waxes are generally prepared by melting a carboxylic acid ester of a polyhydric alcohol, admixing phosphorus pentoxide into the melt, then admixing a silicate or silane into the melt, and cooling to solidify the resulting acid releasing wax. The carboxylic acid ester of a polyhydric alcohol is preferably a glycerol ester or glycol ester including, for example, an alkylene glycol carboxylate such as propylene glycol monostearate, glycerol monostearate, or glycerol distearate. Propylene glycol monostearate is most preferred because it does not foam excessively or obstruct nozzles or other fluid transport equipment when preparing the acid releasing wax, or the powders or when incorporating the powders into polymer films or other materials as end products. A substance that is capable of reacting with the silicate or silane to form P—O—Si or C(O)—O—Si bonds in the acid releasing wax can be substituted for phosphorus pentoxide, such as monostearyl diethylphosphate. A process for preparing a phosphosilicic anhydride acid releasing wax using monostearyl diethylphosphate can be performed with reference to Ralph Iler, "Chemistry of Silica: Solubility, Polymerization, Colloid and Surface Properties in Biochemistry," J. Wiley & Sons, N.Y., p. 297 (1979). Preferred silicates or silanes include tetraalkylsilicates such as tetraethyl orthosilicate, alkyl silanes, and monoalkoxy silanes. The preparation of representative acid releasing waxes is described in Examples 1 and 4 below. The process of preparing the acid releasing waxes is further described in copending Wellinghoff et al. U.S. patent application Ser. No. 08/858,859 (attorney docket no. BTEC 9479), filed May 19, 1997 and entitled "Compositions for Sustained Release of a Gas," which is incorporated herein by reference.

Applications for the powders are numerous. The powders can be used in most any environment where exposure to moisture can occur. The powders can also be impregnated, melt processed, or otherwise incorporated into a variety of materials to provide films and coatings for a wide range of end use applications.

Gas-releasing powders can be used to retard, kill, prevent or control microbiological contamination on a surface of a material, within the material or in the atmosphere surrounding the material by exposing a surface of a material to a powder of the invention, and exposing the surface to moisture to generate and release a biocidal gas from the powder into the atmosphere surrounding the surface. In an alternative embodiment, microbiological contamination is retarded, killed, prevented or controlled on a surface of a material, within the material or in the atmosphere surrounding the material by placing the material adjacent a powder of the invention, and exposing the powder to moisture to release a biocidal gas from the powder into the atmosphere surrounding the material.

The gas-releasing powders can also be used to deodorize a surface of a material or the atmosphere surrounding the material by exposing a surface of a material to a powder of the invention, and exposing the surface to moisture to generate and release a deodorizing gas from the powder into the atmosphere surrounding the surface. In another embodiment, a surface of a material or the atmosphere surrounding the material is deodorized by placing the material adjacent to the powder, and exposing the powder to moisture to release a deodorizing gas from the powder into the atmosphere surrounding the material.

The gas-releasing powders can also be used to retard, prevent or control chemotactic attraction of an organism to a material by exposing a surface of a material to a powder of the invention, and exposing the surface to moisture to generate and release an odor-masking gas from the powder into the atmosphere surrounding the surface. In another embodiment, chemotactic attraction of an organism to a material is retarded, prevented or controlled by placing the material adjacent to the powder, and exposing the powder to moisture to release an odor-masking gas from the powder into the atmosphere surrounding the material.

In the above methods, the surface of the material can be impregnated with the powder, the powder can be admixed with the material, the powder can be enclosed within a gas-permeable container, or the material and the powder can be enclosed within a container. When the powder is enclosed within a container, the container can be hermetically sealed, or partially sealed such that some gas leaks from the container.

The chlorine dioxide-releasing powder, for example, can be impregnated into containers used to store food products, soap, laundry detergent, documents, clothing, paint, seeds, medical instruments, devices and supplies, personal care products, medical or biological waste, athletic shoes, footwear, and refuse. A packet, sachet bag, "tea bag" or other gas-permeable container of the powder can be included in a storage container to provide a chlorine dioxide microatmosphere upon activation. The chlorine dioxide-releasing powder can also be impregnated into a paper or polymeric material (e.g., a shower mat, shoe liners, inserts or insoles, bandage material, a meat cutting board, a food wrapper, a food packaging tray, or a seed packet); admixed with a material to create a microatmosphere of chlorine dioxide about the material (e.g., soil); or admixed with other powders to kill microorganisms or deodorize (e.g., foot powders, bath powders, powders used in treating jock itch).

In addition to deodorization to neutralize malodors, the powders can be used to retard, prevent or control chemotaxis (i.e., the attraction of a living organism to a chemical substance). For example, odors from food can attract insects to the food. When the food is adjacent a powder of the invention that releases an odor-masking gas, the odor released from food is indistinct or imperceptible to the insects.

The following examples are presented to describe preferred embodiments and utilities of the present invention and are not meant to limit the present invention unless otherwise stated in the claims appended hereto.

EXAMPLE 1

In order to make a hydrophobic propylene glycol monostearate acid releasing wax on a laboratory scale, propylene glycol monostearate (200 g) was melted in a dry, stoppered, 2-liter schlenk at 50°–60° C. using a heating mantle. The melt was stirred at constant temperature under reduced pressure for three to four hours to remove residual moisture. When bubbling of the melt under vacuum ceased, the schlenk was flushed and maintained with dry nitrogen gas.

Phosphorus pentoxide (27.7 g) was loaded into a powder addition funnel in a glove bag continuously purged with dry nitrogen. The funnel was connected to the schlenk under flowing nitrogen, and the phosphorus pentoxide was gradually added to the melt using a screw feeder over three or four hours as the melt was stirred rapidly at 50°–60° C. under dry nitrogen. After the addition, the melt was stirred under dry nitrogen gas for at least four hours.

Tetraethyl orthosilicate (TEOS; 39 ,ml) was then added slowly over 40 minutes using an addition funnel. Ethanol by-product was vented through a septum and needle inserted at the top of the addition funnel. After the TEOS addition, remaining ethanol was pumped off under reduced pressure for about 12 hours while minimizing foaming and maintaining a temperature sufficient to volatilize ethanol condensed on the schlenk walls. The resulting propylene glycol monostearate acid releasing wax was then allowed to solidify at room temperature in the glove bag under dry nitrogen.

EXAMPLE 2

A chlorine dioxide-releasing powder was prepared on a laboratory scale. Sodium chlorite flakes (Vulcan Chemicals) were ground to a powder and vacuum dried overnight in a schlenk. Sodium chlorite (10 g), sodium sulfate (775 g; less than 125 μm particle size), the propylene glycol monostearate acid releasing wax of Example 1 (130 g), and Petrowax 3040 microcrystalline wax (90 g) were each placed in a flask and stoppered inside a large glove bag with a Ross mixer under dry nitrogen gas. The mixing bowl was heated to 53° C. with a circulating bath. The glove bag and mixing bowl were purged with dry nitrogen. The Petrowax was then added to the bowl and melted. The sodium chlorite was added to the melted wax and mixed for two minutes. 400 g of the sodium sulfate was added and mixed for two minutes, and then the propylene glycol monostearate acid releasing wax was added and mixed for two minutes. The remaining sodium sulfate was added and mixed for five minutes. The product was collected in an airtight bag under nitrogen with desiccant and cooled overnight The cooled material was cryogenically ground to a powder and stored.

EXAMPLE 3

Another chlorine dioxide-releasing powder was prepared on a laboratory scale. Sodium chlorite flakes (Vulcan Chemicals) were ground to a powder and vacuum dried overnight in a schlenk. Sodium chlorite (10 g), calcium sulfate (775 g), the propylene glycol monostearate acid releasing wax of Example 1 (130 g), and Petrowax 3040 microcrystalline wax (90 g) were each placed in a flask and stoppered inside a large glove bag with a Ross mixer under dry nitrogen gas. The mixing bowl was heated to 53° C. with a circulating bath. The glove bag and mixing bowl were purged with dry nitrogen. The Petrowax was then added to the bowl and melted. The sodium chlorite was added to the melted wax and mixed for three minutes Half of the calcium sulfate was added and mixed for three minutes, and then the propylene glycol monostearate acid releasing wax was added and mixed for two minutes. The remaining calcium sulfate was added and mixed for five minutes. The product was collected in an airtight bag under nitrogen with desiccant and cooled overnight. The cooled material was cryogenically ground to a powder and stored

EXAMPLE 4

In order to make a hydrophobic propylene glycol monostearate acid releasing wax on a commercial scale, propylene glycol monostearate (1225.5 lbs.) was melted at 55° C. using oil heating in a stainless steel stirred tank jacketed reactor with internal cooling coils and a reflux condenser/receiver system. Powdered phosphorus pentoxide (170.2 lbs.) was introduced gradually over three to four hours with cooling. After the reaction proceeded for four to six hours at 55° C., tetraethyl orthosilicate (221.3 lbs) was added to the tank and allowed to react for 12 hours under vacuum. The propylene glycol monostearate acid releasing wax was collected from the bottom of the reactor and allowed to solidify at room temperature.

EXAMPLE 5

A powder providing sustained release of chlorine dioxide was prepared by melting Petrowax 3040 microcrystalline wax (90 g) in a planetary mixer. Sodium chlorite (10 g) was added to the melted wax and mixed for about two minutes. Sodium sulfate (385 g) was added and mixed for about two minutes. Propylene glycol monostearate acid releasing wax of Example 4 (130 g) was then added and mixed for about two minutes. Sodium sulfate (385 g) was poured into the mixer and mixed for about 5 minutes. The product was collected under dry conditions and cooled at room temperature overnight The cooled material was cryogenically ground to a powder and stored.

FIG. 2 shows the chlorine dioxide release rate from the powder. Controlled release over several days is accomplished at varying temperature and humidity conditions ranging from about 70°–80° F. and about 25–50% relative humidity. Chlorine dioxide release rates are dependent on both temperature and relative humidity.

EXAMPLE 6

A powder providing sustained release of chlorine dioxide was prepared by melting Petrowax 3040 microcrystalline wax (90 g) in a planetary mixer. Sodium chlorite (40 g) was added to the melted wax and mixed for about two minutes. Sodium sulfate (155 g) was added and mixed for about two minutes. Propylene glycol monostearate acid releasing wax of Example 4 ; (560 g) was then added and mixed for about two minutes. Sodium sulfate (155 g) was poured into the mixer and mixed for about 5 minutes. The product was collected under dry conditions and cooled at room temperature overnight. The cooled material was cryogenically ground to a powder and stored.

Figure 3:
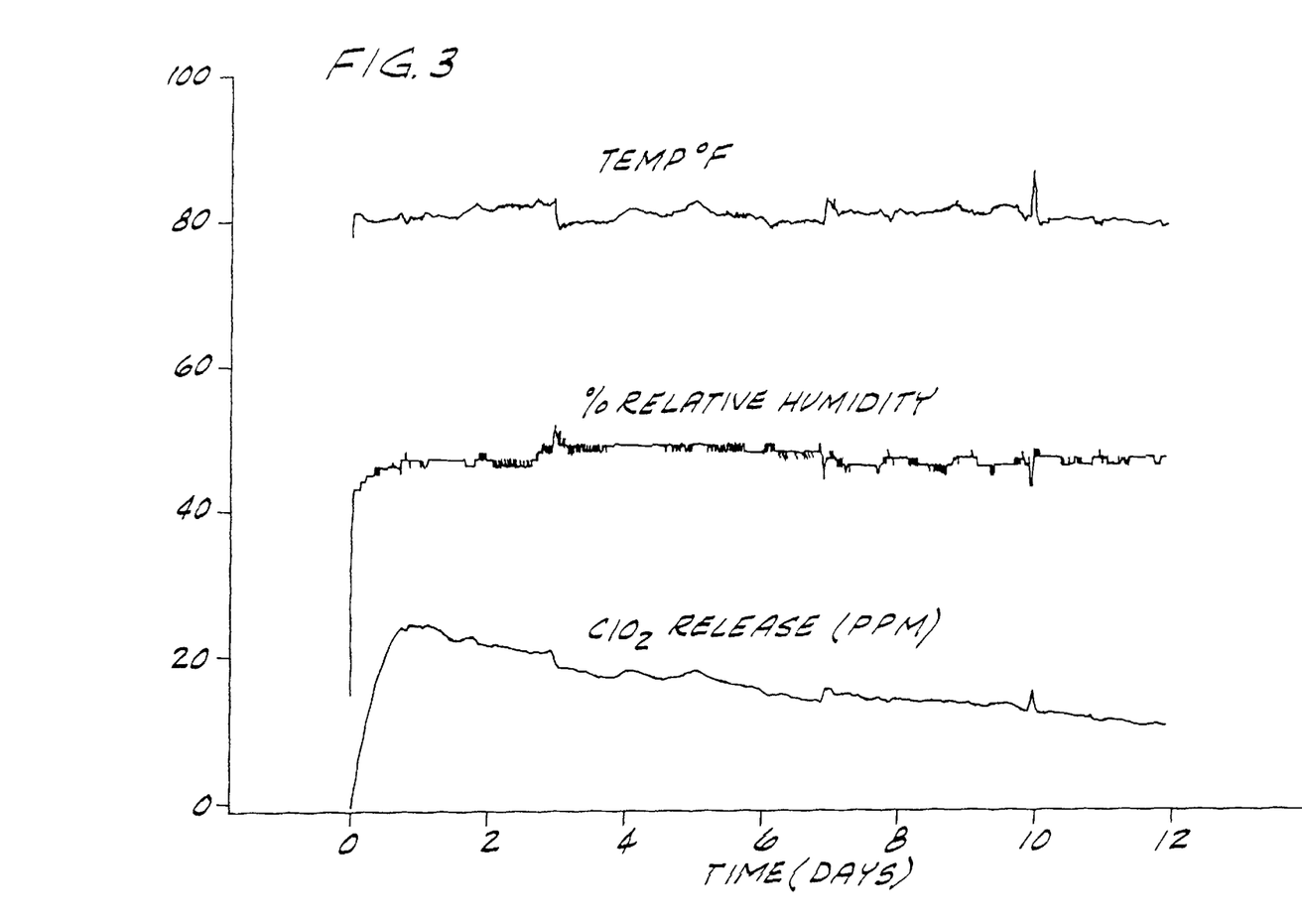

FIG. 3 shows the chlorine dioxide release rate from 7.0 g of the powder. Controlled release over several days is accomplished at about 80° F. and 45% relative humidity.

EXAMPLE 7

A powder providing sustained release of carbon dioxide was prepared by melting Petrowax 3040 microcrystalline wax (90 g) in a planetary mixer. Sodium bicarbonate (40 g) was added to the melted wax and mixed for about two minutes. Sodium sulfate (155 g) was added and mixed for about two minutes. Propylene glycol monostearate acid releasing wax of Example 4 (560 g) was then added and mixed for about two minutes. Sodium sulfate (155 g) was poured into the mixer and mixed for about 5 minutes. The product was collected under dry conditions and cooled at room temperature overnight. The cooled material was cryogenically ground to a powder and stored

EXAMPLE 8

A powder providing sustained release of sulfur dioxide was prepared by melting Petrowax 3040 microcrystalline wax (90 g) in a planetary mixer. Sodium bisulfite (50.8 g; 58 wt. % $SO_2$ from Aldrich) was added to the melted wax and mixed for about two minutes. Sodium sulfate (300 g) was added and mixed for about two minutes. Propylene glycol monostearate acid releasing wax of Example 4 (560 g) was then added and mixed for about two minutes. The product was collected under dry conditions and cooled at room temperature overnight. The cooled material was cryogenically ground to a powder and stored.

Sulfur dioxide released from 1.03 g of the powder was measured by placing the powder in a seven cm path length Perkin-Elmer gas cell of volume 26 $cm^3$ and injecting a small amount of water to effectively bring the relative humidity to 100%. Sulfur dioxide concentration was determined via infrared absorption spectroscopy at a time period following the water injection. The results are shown in Table 1 below:

TABLE 1

| Time (min) | Concentration ($10^3$ ppm) |
| --- | --- |
| 20 | 5.05 |
| 44 | 7.48 |
| 85 | 7.88 |
| 125 | 6.47 |
| 48 hours | 1.01 |

EXAMPLE 9

A powder providing sustained release of chlorine dioxide is prepared by melting a carboxylate of a poly α-hydroxy alcohol such as sorbitan monostearate in a planetary mixer. A chlorite anion source such as sodium chlorite is added to the melt and mixed for about two minutes. Sodium sulfate is then added and mixed for about two minutes. The product is collected under dry conditions and cooled at room temperature overnight. The cooled material is cryogenically ground to a powder and stored.

A precursor of such a powder was formed by melting sorbitan monostearate in a planetary mixer, adding sodium chlorite to the melt and mixing for about two minutes. The melt was white after addition of sodium chlorite, indicating that chlorine dioxide was not generated in the melt. A color change from white to yellow was observed as the melt was heated, indicating generation of chlorine dioxide in the melt. Observations are reported below:

TABLE 2

| No. | ARA Wt.[1] | $NaClO_2$ Wt. | T (°C.)[2] | t (min)[3] | color[4] | dry $N_2$[5] |
| --- | --- | --- | --- | --- | --- | --- |
| 1 | 10 g (90.7%) | 1.0 g (9.3%) | 65 | 30 | BY | Yes |
| 2 | 5.1 g (90.8%) | 0.51 g (9.2%) | 60 | 10 | SY | Yes |
| 3 | 5.0 g (90.9%) | 0.50 g (9.1%) | 61 | 40 | SY | No |
| 4 | 2.0 g (90.4%) | 0.22 g (9.6%) | 61 | 5 | W | No |
| 5 | 1.0 g (90.8%) | 0.10 g (9.2%) | 62–65 | 10 | W | No |
|   |   |   |   | 30 | W |   |
|   |   |   |   | 50 | BY |   |
| 6 | 3.0 g (90.8%) | 0.30 g (9.2%) | 62 | 4 | SY | No |
| 7 | 3.0 g (89.9%) | 0.34 g (10.1%) | 65 | 5 | W | No |
|   |   |   |   | 8 | W |   |
|   |   |   |   | 10 | SY |   |

[1]ARA = acid releasing agent (i.e., sorbitan monostearate)
[2]Temperature at which melt was heated
[3]Time period after which color of melt was observed
[4]Color observed: BY (Bright Yellow); SY (Slight Yellow); W (White)
[5]Whether dry nitrogen atmosphere was used during preparation Chlorine dioxide was not released from preparation nos. 5 and 7 until after thirty minutes and eight minutes, respectively. Thus, sorbitan monostearate is a viable acid releasing acid for use in preparing powders of the invention.

While the invention is susceptible to various modifications and alternative forms, specific embodiments thereof have been shown by way of example in the drawings and have been described herein in detail It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A powder for sustained release of a gas comprising:
   a hydrophilic core;
   a hydrophobic layer on an outer surface of the hydrophilic core, the hydrophobic layer containing an acid releasing agent; and
   particles in contact with the hydrophobic layer, the particles containing an anhydrous material capable of binding with water;
   the core, the particles, and the hydrophobic layer being substantially free of water; the core being capable of generating and releasing a gas after hydrolysis of the acid releasing agent.

2. The powder of claim 1 wherein the hydrophilic core contains chlorite anions, bisulfite anions, cyanide anions, nitrite anions, hypochlorite anions, or hydrosulfide anions.

3. The powder of claim 2 wherein the hydrophilic core contains an alkali metal chlorite, an alkaline-earth metal chlorite, a chlorite salt of a transition metal ion or a protonated primary, secondary, tertiary or quaternary amine, an alkali metal bisulfite, an alkaline-earth metal bisulfite, a bisulfite salt of a transition metal ion or a protonated primary, secondary, tertiary or quaternary amine, an alkali metal hydrosulfide, an alkaline-earth metal hydrosulfide, a hydrosulfide salt of a transition metal ion or a protonated primary, secondary, tertiary or quaternary amine, an alkali metal nitrite, an alkaline-earth metal nitrite, a nitrite salt of a transition metal ion or a protonated primary, secondary, tertiary or quaternary amine, an alkali metal hypochlorite; an alkaline-earth metal hypochlorite, a hypochlorite salt of a transition metal ion or a protonated primary, secondary, tertiary or quaternary amine, an alkali metal cyanide, an alkaline-earth metal cyanide, or a cyanide salt of a transition metal ion or a protonated primary, secondary, tertiary or quaternary amine.

4. The powder of claim 2 wherein the hydrophilic core contains a sodium, potassium, calcium, lithium or ammonium salt of a chlorite, bisulfite, hydrosulfide, nitrite, hypochlorite, or cyanide.

5. The powder of claim 2 wherein the gas is chlorine dioxide, sulfur dioxide, hydrogen sulfide, hydrocyanic acid, nitrogen dioxide, nitric oxide, dichlorine monoxide, or chlorine.

6. The powder of claim 1 wherein the hydrophobic layer further includes microcrystalline wax, paraffin wax, synthetic wax, or a polymer.

7. The powder of claim 6 wherein the hydrophobic layer further includes a dispersant selected from the group consisting of an amide of a carboxylate, polyvinylpyrrolidone copolymer, polyvinyl acetate, polyvinyl alcohol, and metal carboxylate.

8. The powder of claim 1 wherein the acid releasing agent is an acid releasing wax.

9. The powder of claim 8 wherein the acid releasing wax has the formula:

wherein each R is individually selected from hydrogen, hydroxy, alkyl, alkenyl, or —OC(O)R'; R' is a $C_4$ to $C_{27}$ alkyl or $C_4$ to $C_{27}$ alkenyl; x is an integer from 1 to 30; y is an integer from 0 to 30; and z is an integer from 0 to 30.

10. The powder of claim 1 wherein the acid releasing agent includes a carboxylic acid, an ester, an anhydride, an acyl halide, phosphoric acid, a phosphate ester, a trialkylsilyl phosphate ester, a dialkyl phosphate, sulfonic acid, a sulfonic acid ester, a sulfonic acid chloride, a phosphosilicic anhydride, a carboxylate of a poly α-hydroxy alcohol, a phosphosilicate, or a phosphosiloxane.

11. The powder of claim 8 wherein the particles contain sodium sulfate, calcium sulfate, ferrous sulfate, magnesium sulfate, calcium chloride, moisture-depleted silica gel, alumina, zeolites, bentonite clay, kaolin clay, potassium permanganate, molecular sieves or an oxygen-scavenging salt.

12. The powder of claim 1 wherein at least about $1.0 \times 10^{-6}$ mole chlorine dioxide/cm$^2$ is released from the powder for a period of at least one week after hydrolysis of the acid releasing agent.

13. The powder of claim 1 wherein the hydrophobic layer is continuous.

14. A powder for sustained release of a gas comprising:

a hydrophilic core;

a first hydrophobic layer containing an acid releasing agent;

a second hydrophobic layer between the first hydrophobic layer and the hydrophilic core; and particles in contact with the first hydrophobic layer, the particles containing an anhydrous material capable of binding with water;

the core, the particles, the first hydrophobic layer and the second hydrophobic layer being substantially free of water; the core being capable of generating and releasing a gas after hydrolysis of the acid releasing agent.

15. The powder of claim 14 wherein the hydrophilic core contains chlorite anions, bisulfite anions, cyanide anions, nitrite anions, hypochlorite anions, or hydrosulfide anions.

16. The powder of claim 15 wherein the hydrophilic core contains an alkali metal chlorite, an alkaline-earth metal chlorite, a chlorite salt of a transition metal ion or a protonated primary, secondary, tertiary or quaternary amine, an alkali metal bisulfite, an alkaline-earth metal bisulfite, a bisulfite salt of a transition metal ion or a protonated primary, secondary, tertiary or quaternary amine, an alkali metal hydrosulfide, an alkaline-earth metal hydrosulfide, a hydrosulfide salt of a transition metal ion or a protonated primary, secondary, tertiary or quaternary amine, an alkali metal nitrite, an alkaline-earth metal nitrite, a nitrite salt of a transition metal ion or a protonated primary, secondary, tertiary or quaternary amine, an alkali metal hypochlorite, an alkaline-earth metal hypochlorite, a hypochlorite salt of a transition metal ion or a protonated primary, secondary, tertiary or quaternary amine, an alkali metal cyanide, an alkaline-earth metal cyanide, or a cyanide salt of a transition metal ion or a protonated primary, secondary, tertiary or quaternary amine.

17. The powder of claim 15 wherein the hydrophilic core contains a sodium, potassium, calcium, lithium or ammonium salt of a chlorite, bisulfite, hydrosulfide, nitrite, hypochlorite, or cyanide.

18. The powder of claim 14 wherein the gas is chlorine dioxide, sulfur dioxide, hydrogen sulfide, hydrocyanic acid, nitrogen dioxide, nitric oxide, dichlorine monoxide, or chlorine.

19. The powder of claim 14 wherein the first hydrophobic layer and the second hydrophobic layer each individually contains microcrystalline wax, paraffin wax, synthetic wax, or a polymer.

20. The powder of claim 19 wherein the first hydrophobic layer or the second hydrophobic layer further includes a dispersant selected from the group consisting of an amide of a carboxylate, polyvinylpyrrolidine copolymer, polyvinyl acetate, polyvinyl alcohol,or metal carboxylate.

21. The powder of claim 14 wherein the acid releasing agent is an acid releasing wax.

22. The powder of claim 21 wherein the acid releasing wax has the formula:

wherein G has the formula —(CR$_2$)$_x$—CR$_3$ or wherein each R is individually selected from hydrogen, hydroxy, alkyl, alkenyl, or —OC(O)R'; R' is a C$_4$ to C$_{27}$ alkyl or C$_4$ to C$_{27}$ alkenyl; x is an integer from 1 to 30; y is an integer from 0 to 30; and z is an integer from 0 to 30.

23. The powder of claim 14 wherein the acid releasing agent includes a carboxylic acid, an ester, an anhydride, an acyl halide, phosphoric acid, a phosphate ester, a trialkylsilyl phosphate ester, a dialkyl phosphate, sulfonic acid, a sulfonic acid ester, a sulfonic acid chloride, a phosphosilicic anhydride, a carboxylate of a poly α-hydroxy alcohol, a phosphosilicate, or a phosphosiloxane.

24. The powder of claim 21 wherein the particles contain sodium sulfate, calcium sulfate, ferrous sulfate, magnesium sulfate, calcium chloride, moisture-depleted silica gel, alumina, zeolites, bentonite clay, kaolin clay, potassium permanganate, molecular sieves or an oxygen-scavenging salt.

25. The powder of claim 14 wherein at least about $1.0 \times 10^{-6}$ mole chlorine dioxide/cm$^2$ is released from the powder for a period of at least one week after hydrolysis of the acid releasing agent.

26. The powder of claim 14 wherein the first hydrophobic layer or the second hydrophobic layer is continuous.

27. A powder for sustained release of a gas comprising:

a hydrophilic core containing chlorite anions;

a first hydrophobic layer containing an acid releasing wax having the formula wherein G has the formula —(CR$_2$)$_x$—CR$_3$ or CR$_3$ wherein each R is individually selected from hydrogen, hydroxy, alkyl, alkenyl, or —OC(O)R'; R' is a C$_4$ to C$_{27}$ alkyl or C$_4$ to C$_{27}$ alkenyl; x is an integer from 1 to 30; y is an integer from 0 to 30; and z is an integer from 0 to 30;

a second hydrophobic layer between the first hydrophobic layer and the hydrophilic core, the second hydrophobic layer containing microcrystalline wax, paraffin wax, synthetic wax, or a polymer; and particles in contact with the first hydrophobic layer, the particles containing an anhydrous material capable of binding with water;

the core, the particles, the first hydrophobic layer and the second hydrophobic layer being substantially free of water; the core being capable of releasing chlorine dioxide gas upon hydrolysis of the acid releasing agent.

28. A method of retarding, killing, preventing or controlling microbiological contamination on a surface of a material, within the material or in the atmosphere surrounding the material, comprising exposing a surface of a material to a powder of claim 1, and exposing the surface to moisture to generate and release a biocidal gas from the powder into the atmosphere surrounding the surface.

29. The method of claim 28 wherein the surface of the material is impregnated with the powder.

30. The method of claim 28 wherein the material and the powder are enclosed within a container.

31. The method of claim 30 wherein the container is hermetically sealed.

32. The method of claim 30 wherein the container is partially sealed.

33. A method of retarding, killing, preventing or controlling microbiological contamination on a surface of a material, within the material or in the atmosphere surrounding the material, comprising placing the material adjacent a powder of claim 1, and exposing the powder to moisture to release a biocidal gas from the powder into the atmosphere surrounding the material.

34. The method of claim 33 wherein the powder is enclosed within a gas-permeable container.

35. The method of claim 33 wherein the powder is admixed with the material.

36. The method of claim 33 wherein the material and the powder are enclosed within a container.

37. The method of claim 36 wherein the container is hermetically sealed.

38. The method of claim 36 wherein the container is partially sealed.

39. A method of deodorizing a surface of a material or the atmosphere surrounding the material, comprising exposing a surface of a material to a powder of claim 1, and exposing the surface to moisture to generate and release a deodorizing gas from the powder into the atmosphere surrounding the surface.

40. The method of claim 39 wherein the surface of the material is impregnated with the powder.

41. The method of claim 39 wherein the material and the powder are enclosed within a container.

42. The method of claim 41 wherein the container is hermetically sealed.

43. The method of claim 41 wherein the container is partially sealed.

44. A method of deodorizing a surface of a material or the atmosphere surrounding the material, comprising placing the material adjacent a powder of claim 1, and exposing the powder to moisture to release a deodorizing gas from the powder into the atmosphere surrounding the material.

45. The method of claim 44 wherein the powder is enclosed within a gas-permeable container.

46. The method of claim 44 wherein the powder is admixed with the material.

47. The method of claim 44 wherein the material and the powder are enclosed within a container.

48. The method of claim 47 wherein the container is hermetically sealed.

49. The method of claim 47 wherein the container is partially sealed.

50. A method of retarding, preventing or controlling chemotactic attraction of an organism to a material, comprising exposing a surface of a material to a powder of claim 1, and exposing the surface to moisture to generate and release an odor-masking gas from the powder into the atmosphere surrounding the surface.

51. The method of claim 50 wherein the surface of the material is impregnated with the powder.

52. The method of claim 50 wherein the material and the powder are enclosed within a container.

53. The method of claim 52 wherein the container is hermetically sealed.

54. The method of claim 52 wherein the container is partially sealed.

55. A method of retarding, preventing or controlling chemotactic attraction of an organism to a material, comprising placing the material adjacent a powder of claim 1, and exposing the powder to moisture to release an odor-masking gas from the powder into the atmosphere surrounding the material.

56. The method of claim 55 wherein the powder is enclosed within a gas-permeable container.

57. The method of claim 55 wherein the powder is admixed with the material.

58. The method of claim 55 wherein the material and the powder are enclosed within a container.

59. The method of claim 58 wherein the container is hermetically sealed.

60. The method of claim 58 wherein the container is partially sealed.

61. A process for preparing a powder providing sustained release of a gas, the process comprising:

providing a hydrophobic liquid containing an acid releasing agent;

admixing hydrophilic particles containing anions into the hydrophobic liquid to form coated hydrophilic particles;

admixing anhydrous particles with the coated hydrophilic particles to form a product;

cooling the product; and fragmenting the product to form a powder.

62. The process of claim 61 wherein a dispersant is admixed with the hydrophobic liquid before admixing with the hydrophilic particles.

63. A process for preparing a powder providing sustained release of a gas, the process comprising:

providing a hydrophobic liquid;

admixing hydrophilic particles containing anions into the hydrophobic liquid to form coated hydrophilic particles;

admixing a hydrophobic material containing an acid releasing agent with the coated hydrophilic particles to form an intermediate powder;

admixing the intermediate powder with anhydrous particles to form a product;

cooling the product; and fragmenting the product to form a powder.

64. The process of claim 63 wherein a dispersant is added to the hydrophilic liquid before admixing with the hydrophilic particles.

65. The process of claim 63 wherein anhydrous particles are admixed with the coated hydrophilic particles before the hydrophobic material is added to form the intermediate powder.

* * * * *

UNITED STATES PATENT AND TRADEMARK OFFICE
CERTIFICATE OF CORRECTION

PATENT NO. : 5,888,528
DATED : March 30, 1999
INVENTOR(S) : Wellinghoff et al.

It is certified that error appears in the above-identified patent and that said Letters Patent is hereby corrected as shown below:

<u>Title page,</u>
Item [73], Assignee, should read -- Bernàrd Technologies, Inc., Chicago, Ill.; and Southwest Research Institute, San Antonio, TX --.

Signed and Sealed this

Fifteenth Day of November, 2005

JON W. DUDAS
*Director of the United States Patent and Trademark Office*